United States Patent [19]
Halbert et al.

[11] Patent Number: 4,642,285
[45] Date of Patent: * Feb. 10, 1987

[54] SANDWICH EIA FOR ANTIGEN

[75] Inventors: Seymour P. Halbert, Miami; Milton Anken, N. Miami Beach, both of Fla.

[73] Assignee: Diamedix Corporation, Miami, Fla.

[*] Notice: The portion of the term of this patent subsequent to Oct. 2, 2001 has been disclaimed.

[21] Appl. No.: 606,122

[22] Filed: May 2, 1984

Related U.S. Application Data

[63] Continuation of Ser. No. 617,743, Sep. 29, 1975, Pat. No. 4,474,878.

[51] Int. Cl.$^4$ .................. G01N 33/53; G01N 33/535; G01N 33/545; G01N 33/576
[52] U.S. Cl. .......................................... 435/7; 435/21; 436/531; 436/532; 436/820
[58] Field of Search .................. 435/7, 12, 19, 20, 21, 435/22, 25; 436/531

[56] References Cited

U.S. PATENT DOCUMENTS

| | | |
|---|---|---|
| Re. 29,169 | 4/1977 | Schuurs et al. |
| 3,646,346 | 2/1972 | Catt |
| 3,654,090 | 4/1972 | Schuurs et al. |
| 3,791,932 | 2/1974 | Schuurs et al. |
| 3,817,837 | 6/1974 | Rubenstein et al. |
| 3,839,153 | 10/1974 | Schuurs et al. |
| 3,852,157 | 12/1974 | Rubenstein et al. |
| 3,867,517 | 2/1975 | Ling |
| 3,876,504 | 4/1975 | Koffler |
| 3,896,217 | 7/1975 | Johnson |
| 3,896,218 | 7/1975 | Charm et al. |
| 3,905,767 | 9/1975 | Morris et al. |
| 4,016,043 | 4/1977 | Schuurs |
| 4,034,072 | 7/1977 | Mjos et al. |
| 4,154,795 | 5/1979 | Thorne |

FOREIGN PATENT DOCUMENTS

| | | |
|---|---|---|
| 2277564 | 2/1976 | France |
| 1310923 | 3/1973 | United Kingdom |
| 1390617 | 4/1975 | United Kingdom |

OTHER PUBLICATIONS

Bonacker & Hevey, "Enzyme Immunoassays", Chapter 12 of Serum Abnormalities–Diagnostic and Clinical Aspects, Ed., Ritzmamann & Daniels (1975) Little, Brown & Co.).

List continued on next page.

*Primary Examiner*—Sidney Marantz
*Attorney, Agent, or Firm*—Davis Hoxie Faithfull & Hapgood

[57] ABSTRACT

A sensitive direct immunoassay system is provided for the detection of an antigen in body fluids. A single antibody which reacts with an antigen or antigens and which is bonded to an insoluble member, is incubated with a test sample. During this first period of incubation a portion of an antigen present in the test sample will combine with the antibody immobilized on the insoluble member. The antibody bonded member, to which antigen is attached, is then washed and incubated with an enzyme tagged antibody reagent. During the second incubation, the tagged antibody reacts with antigen fixed to the antibody member in the first incubation. Thus, an immobilized "sandwich" is formed of an insoluble member- antibody-antigen-enzyme tagged antibody. After the second incubation, the member is washed again to remove unreacted enzyme antibody reagent. The member is then exposed to a substrate which is converted by the enzyme to produce an end product. The tagged antibody reagent will be fixed in the second incubation only if antigen was present in the sample. The amount of enzyme tagged antitbody fixed is proportional to the amount of antigen or antigens present in the test sample up to the maximum capacity of the test. The concentration of the end product, and hence the amount of antigen or antigens, is determined by a spectrophotometer which measures the optical absorption of light by the end product. This readout is then compared against a standard value for both antigen negative and antigen positive samples.

18 Claims, 8 Drawing Figures

OTHER PUBLICATIONS

Belanger et al., Clin, Chim, Acta, vol. 48, pp. 15–17 (1973).
Brzosko, W. J. et al., The Lancet, 1058, May 16, 1970.
Catt et al., *J. Lab. and Clin Med.*, vol. 70, pp. 820–822 (1967).
Engvall, E. et al., *The Journal of Immunology*, 109 (1), 129–135 (1972).
Engvall et al., *Biochem, Biophys, Acta.*, vol. 251, pp. 427–434 (1971).
Engvall, E. & Perlmann, P., "Enzyme–linked Immunosorbent Assay ELISA", Protides of the Biological Fluids, proceedings of the 19th Colloquium, 1971, ed. H. Peters, pp. 553–556.
Haberman, Z., klin Chem u. klin, Biochem, 51–55, 8th year Ja. 1970.
Miles, L. E. M. & Hales, C. N. *Nature*, 219, 186–189, Jul. 13, 1968.
Ling et al., *Science*, vol. 180, pp. 203–205 (1973).
Ruitenberg, et al., "Serodiagnosis of Trichinella Spiralis Infections in Pigs by Enzyme–Linked Immunoabsorbent Assays", Bull. Wld. Health., Org., 1974, 51, pp. 108–109.
Salmon, S. E. et al., *The Journal of Immunology*, 103, 129–137, Jul. 1969.
Saunders et al., "Disease Screening with Enzyme–Labelled Antibodies", J. Info. Dis., vol. 129 pp. 362–364, (Mar. '84).
Schuurs et al., The American Journal of the Medical Sciences, 270(1), 173–177 (1975).
Stimson et al., "An immunoassay for a Pregnancy Associated–Macroglobulin Using Antibody–Enzyme Conjugates", FEBS Letters, vol. 47, No. 1, pp. 190–192, (Oct. 1974).
van Weeman and Schuurs, "Immunoassay Using Antibody Enzyme Conjugates", FEBS Letters, vol. 43, No. 2 (July 1974), pp. 215–218.
Engvall & Perlman, "Enzyme–linked Immunosorbent Assay (ELISA) Quantitative Assay of Immunoglobulin G", *Immunochemistry*, vol. 8 (1971), pp. 871–874.

SANDWICH EIA FOR ANTIGEN

CROSS REFERENCE TO RELATED APPLICATIONS

This application is a continuation of application Ser. No. 617,743 filed Sept. 29, 1975, now U.S. Pat. No. 4,474,878.

BACKGROUND OF THE INVENTION (a) Field of the Invention

This invention relates, in general, to a method for detecting the presence of antigens. In particular, it relates to an immunoassay for antigens associated with hepatitis involving the use of an enzyme-tagged antibody which reacts with an antigen to detect the presence of hepatitis.

(b) Description of the Prior Art

Hepatitis, which means "an inflammation of the liver", is due to an infection or obstruction of the bile channels. There are thought to be two varieties of viral hepatitis, one having a longer incubation period than the other. In the past, when a patient contracted hepatitis and had a known parenteral exposure, the hepatitis was termed "serum hepatitis". If the patient did not have a known parenteral exposure and he contracted hepatitis orally it was called "infectious". However, it has been documented that in addition to having overlapping incubation periods, "infectious hepatitis" can be contracted parenterally, and, the so-called "serum hepatitis" can be contracted orally. Thus, although there would appear to be two forms of hepatitis caused by at least two distinct agents, the terms "serum hepatitis" and "infectious hepatitis" should not be used to distinguish them. Accordingly, it has been suggested that the terms "hepatitis A" be used to designate the form most closely resembling "infectious hepatitis", and, the term "hepatitis B" be used to designate the form most closely resembling "serum hepatitis".

The examples appearing in this specification are directed to the detection of the antigen or antigens associated with hepatitis type B. Patients who contract the form most closely resembling serum hepatitis, no matter how contracted, often have these antigens in their blood. At this point, it should be noted that there is no reliable assay for determining the presence of an antigen associated with hepatitis A or an hypothesized hepatitis C. Thus, the examples in this specification are directed to the detection of the presence of those antigens associated with hepatitis B. However, there is no reason why the process of the present invention could not be used to detect the presence of antigens associated with other types of hepatitis once their antigens have been identified.

Contraction of "serum hepatitis" or hepatitis B creates a serious clinical problem that cannot be ignored. Because of the severity of this problem, a variety of test methods for the detection of hepatitis have been developed. These included Micro-Ouchterlony, immunodiffusion, complement fixation, immunoelectro-osmophoresis, haemagglutination and haemagglutination inhibition, electron microscopy, and solid phase radio-immunoassay. See British Medical Bulletin, 1972, Vol. 28, No. 2 (Viral Hepatitis) pages 138–141 for a brief description of each.

Immunoelectro-osmophoresis or counterelectrophoresis (CEP) provides a rapid, simple method for the detection of the hepatitis antigen and its antibody. However, this technique is somewhat less sensitive than, for example, complement fixation. Its principal advantage is that tests can be completed within two hours. However, because of its low sensitivity level CEP is no longer approved by the Food and Drug Administration.

The application of radio-immunoassay (RIA) for routine diagnostic purposes is believed to be somewhat limited, not only because of the relatively complex, specialized, and expensive equipment necessary for conducting the test, but also because of the strict precautions required in handling radio-active isotopes. Isotope tagging presents a serious potential health hazard, requires monitoring and Atomic Energy Commission licensing (for user and manufacturer), and presents waste disposal problems. Nevertheless, this technique is now rather well established for immunoassay.

Immunological methods depend, of course, upon a primary characteristic of all antibodies and antigens, i.e., their ability to react with a specific complimentary antigen or antibody. Thus, if an antibody is added to a serum containing its antigen, the antibody and antigen will complex and may precipitate from the solution. In most of the above-mentioned test methods, the presence of antigens in human sera is detected by making use of this simple fact.

Labeled antibodies have been used previously for identifying various antigens. If an antibody known to be specific for a particular antigen is isolated from the globulin portion of serum or plasma of a host animal which has been stimulated to produce that antibody, it can be labeled or tagged by known means. By conjugating the antibody with a labeling agent, e.g., a physically detectable substance such as a radio isotope, as above-mentioned, or fluorescent chemicals, the presence of the antibody can be detected. Thus, when used diagnostically, if the counterpart antigen is present in some prepared test sample, the labeled antibody will attach itself to that antigen, and the presence of the antigen can be confirmed through detection of the labeled antibody in the sample.

A labeled antibody, for diagnostic purposes, should be made sufficiently specific so that it will react only with those antigens whose detection is desired and without cross-reaction with other closely related antigens which may have quite dissimilar or insignificant consequences. Thus, it is apparent that both the source and the manner of preparation of the antibody is quite critical in any immunoassay.

One manner of detecting hepatitis associated antigen, as earlier mentioned, involves solid phase radio-immunoassay. Such a procedure is disclosed in U.S. Pat. No. 3,867,517. As disclosed therein, in the performance of the assay, a tube well, or insert for use therewith, of molded polystyrene is first coated with antibody. This is accomplished by incubating the member to be coated with an antibody solution. Afterwards, the unknown sample is incubated with the coated well or insert to react the antibody with antigen present in the sample. The well is then washed and incubated with an antibody labeled with the radioactive isotope I-125. It is then again washed to remove any unbonded labeled antibody. Thus, in the event any antigen is present in the test sample, a sandwich is formed from the polystyrene well (or insert), the antibody, the antigen, and the I-125 tagged antibody. The radiation emitted from the I-125 tagged antibody is then counted and compared against a control.

It has also been disclosed that a disc of polytetrofluorethylene onto which is grafted a substituted polystyrene, e.g., isothiocyanostyrene, might be useful in performing radio-immunoassay. This polystyrene is an insoluble material having specifically designed surfaces of protein-reactive groups which may be used to covalently bond proteins to provide a reagent useful in bioassay procedures.

Recently, an important alternative to labeling antibodies with radio-isotopes or fluorescent chemicals has been developed. This involves labeling or tagging an antibody with an enzyme. Such a procedure is described in U.S. Pat. Nos. 3,654,090 and 3,791,932. In Clinica Chemica Acta, 48 (1973) 15–18, an enzyme-linked immunoassay for alphafetoprotein by either the competitive or the sandwich procedure is disclosed.

Compared to radio-immunoassay, enzyme labeling offers several important advantages. For example, every enzyme tagged molecule in the final mixture participates in the readout. On the other hand, only a very small proportion of isotopic atoms in the final mixture undergo decay during readout to participate in the assay. In enzyme tagging, every tag repeatedly participates in readout, by attacking many substrate molecules to form a detectable end product, e.g., up to 100,000 times per minute, hence greatly enhancing sensitivity. An isotope tagged atom decays only once during readout, after which it is lost from participation. An enzyme tagged reagent has a long shelf life; whereas, the isotope tagged reagent is constantly decaying, and presents serious shelf life problems. While there is minimal health hazards associated with using an enzyme tagged reagent, serious potential health hazards are encountered with isotope tagging. Lastly, an immunoassay involving enzyme tagging can use simple, relatively inexpensive equipment for readout. The success of isotope immunoassay, in contrast, is dependent on the efficiency of detecting decay, and hence on the quality of very expensive detection equipment.

Although the finding of an antigen associated with hepatitis in one's blood may not be the equivalent of obtaining a clinical history of hepatitis, investigations have revealed a high incidence of hepatitis infection when a patient has received blood which tests positively for antigens associated with hepatitis. Since decisions on whether to use particular blood units available from a blood center must often be made in a relatively short time period, a sensitive, rapid, easy to perform screening test for hepatitis, without need for expensive equipment, is of extreme importance. Although the various tests used in the past for the detection of the antigens associated with hepatitis have been satisfactory to a degree, they are all attendant with one or more disadvantages.

SUMMARY OF THE INVENTION

This invention broadly involves a direct immunoassay for antigens involving the "sandwich" principle. In the performance of the assay, antigen to be detected is sandwiched between antibody layers which react with it. One antibody layer is covalently linked to an enzyme. The other layer is covalently bonded to an insoluble, water-insuspensible solid carrier. The enzyme is exposed to a chemical substrate which will undergo a chemical change to produce a reaction product in the presence of the enzyme catalyst. The presence of the antigen is determined by determining the presence of the reaction product.

DESCRIPTION OF THE PREFERRED EMBODIMENT

Figure 1:
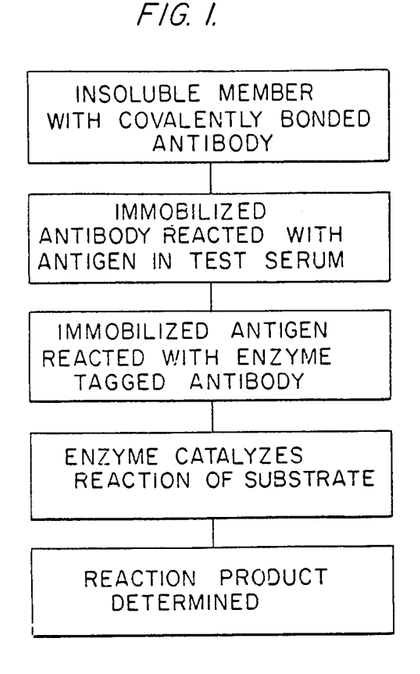
FIG. 1 is a flow chart summarizing the steps of the process of the present invention.

At the outset the invention is described in its broadest overall aspects with a more detailed description following. The method of detecting antigens according to the present invention is carried out in four distinct stages as is illustrated in FIG. 1.

Figure 2:
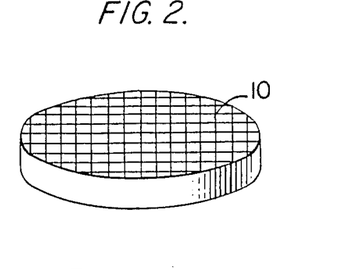
FIG. 2 is a perspective view of an insoluble member useful with the present invention.
Figure 3:
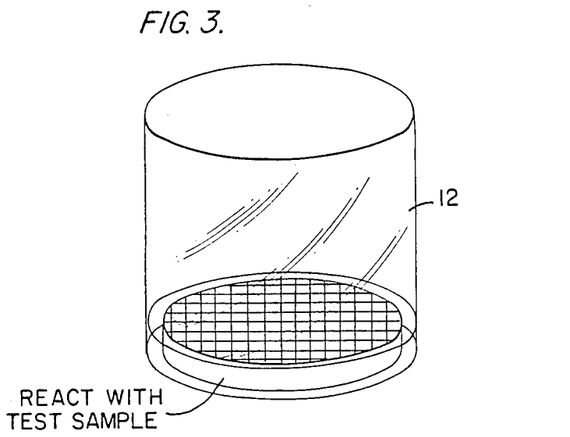
FIGS. 3, 4, and 5 depict three incubation stages of the immunoassay of the present invention.
Figures 4, 5, 6:
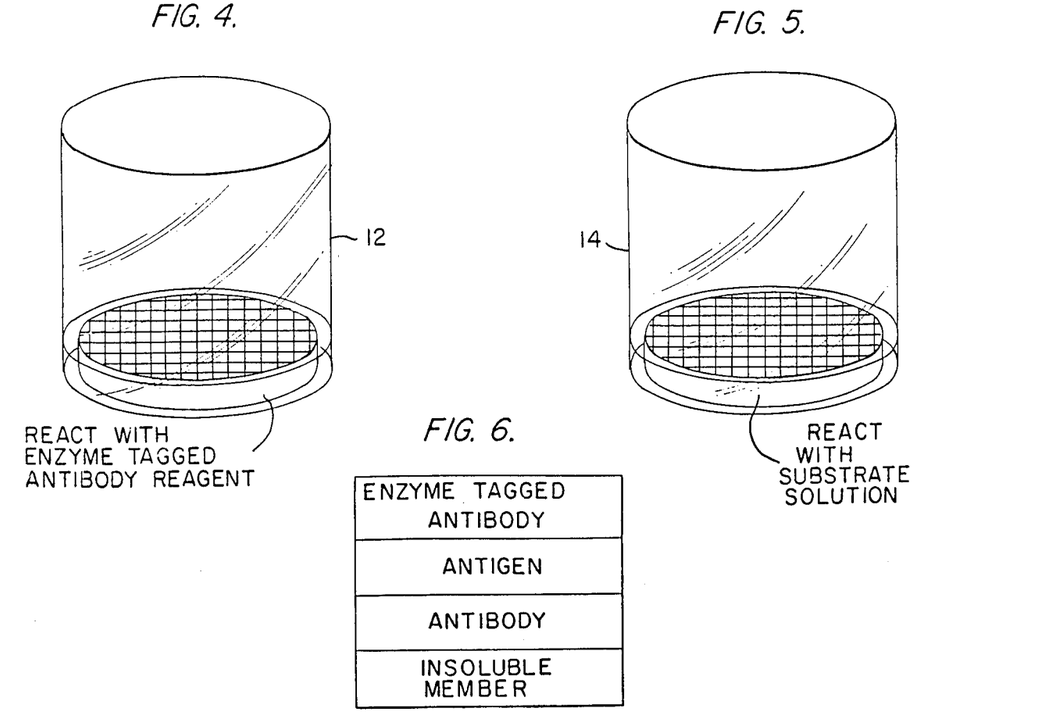
FIG. 6 is a schematic representation showing the "sandwich" structure developed during positive immunoassay of a test sample tested in accordance with the present invention.
Figure 7:
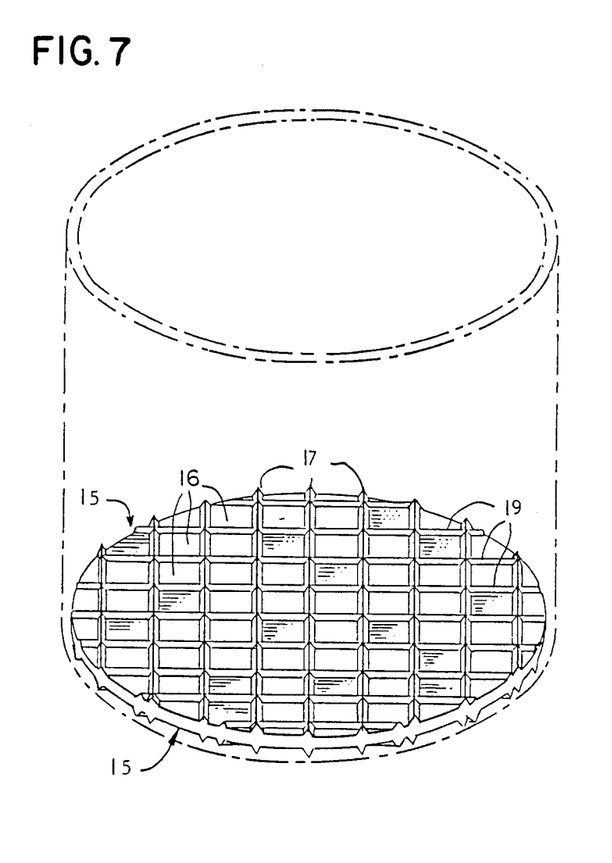
FIG. 7 is a perspective view of a disc useful with the immunoassay of the invention in a vial.

The first stage involves reacting the immobilized antibody on the insoluble member 10 (see FIG. 2) with an antigen present in the test serum as is shown in FIG. 3. This reaction immobilizes antigen, so that on reaction in the next stage with an enzyme tagged antibody, as is shown in FIG. 4, the tagged antibody is also immobilized. As is shown in FIG. 5, the enzyme is exposed to a suitable substrate which is reacted upon by the enzyme to produce changes in color. The color change acts as an indication of the presence of antigens. The last stage involves reading the degree of color and comparing the value obtained with a standard of control.

The various steps taken in preparation of the reagents used in the immunoassay of the present invention follow.

Preparation of Antibody

In order to practice the present invention, it is necessary to provide an antibody that will react with an antigen or antigens. It should be noted that such an antibody exists, and thus, the present invention is not intended to be limited to the use of any particular antibody.

A reactive antibody may be prepared by purifying bleedings from a host animal which has been injected with a known sample of antigen. For example, an antibody which is reactive with an antigen associated with hepatitis may be prepared by the general process disclosed in British Pat. No. 1,387,625. More specific details for preparing an antibody which is reactive with an antigen associated with hepatitis are set forth below.

The preparation of hepatitis antibody depends first of all on obtaining blood which is known to be positive for antigens associated with hepatitis. Consequently, blood units obtained from various sources must first be evaluated to determine their suitability for preparing the immunospecific purified antibody of the invention.

A blood bag segment, containing blood which is believed to be positive for hepatitis antigens, is held at 2°–8° C. in an upright position to allow the blood cells to settle to the lower half. The plasma is separated from the cells and a titer is run on the undiluted plasma and a sample diluted 1:16 in normal saline against a standard antibody by the well-known technique of counterelectrophoresis (CEP). When both the undiluted plasma sample and the 1:16 diluted sample are positive, the blood unit is considered acceptable for use in the preparation of the purified antibody of the invention as described hereinafter.

Portions of antigens isolated from blood units are used for either stimulating antibody production in a host animal or purifying the antibody produced by that animal. The antigens must be subjected to a preliminary isolation process prior to either of the above uses.

The plasma is transferred to a serile vacuum container and clotted by adding a 5M solution of a $CaCl_2$ on the basis of 0.75 ml $CaCl_2$ per 200 ml of plasma. This solution is then incubated at 37° C. in a water bath for one hour or until a clot forms. After a firm clot forms, the plasma is frozen at −20° C. and allowed to thaw at 2°-8° C. to allow clot retraction. The serum is separated from the clot and filtered if necessary, then is ready for preparation of a hepatitis antigen pellet for immunization for use in immunoabsorbent columns.

Preparation of Pellet for Immunization

Hepatitis positive sera which have been subjected to the above process are centrifuged at 10,000 rpm for 30 minutes at 4° C. The supernatant of this centrifugation is distributed into ultra centrifuge tubes and centrifuged in, for example, a Beckman L2-65B ultra-centrifuge, at 40,000 to 50,000 rpm for 4–20 hours at 4° C. The supernatant in each tube is removed and discarded; the pellet, which contains antigens, is given a preliminary rinse with normal (0.15M) saline.

A small volume of normal saline is then added to each centrifuge tube and the contents are subjected to sonication to break up the pellet. The suspensions in the sonicator tubes are then pooled and redistributed equally into clean tubes which are filled with normal saline. This solution is again centrifuged in the Beckman L2-65B centrifuge at 40,000 to 50,000 rpm for 4–20 hours at 4° C., as mentioned above.

The procedure in the preceding paragraph may be repeated 5 or more times.

The pellet material, after removing the supernatant from each centrifuge tube, is pooled in the minimal volume of normal saline. A sample is assayed against a standard hepatitis antibody. If the pellet titers at 1:25 or higher by CEP, it can be used for immunization. The pooled antigen pellet may be divided into 3 ml aliquots and frozen at −20° C. for future use.

Production and Preliminary Purification of Hepatitis Antibody

A sample of the antigen pellet, prepared as described above, is added to an equal volume of FREUND'S complete adjuvant the morning of the immunization and an emulsion is prepared in accordance with procedures well known to those skilled in the art. The antigen is then injected into a host animal, e.g., a horse, in accordance with techniques known per se, to produce hepatitis antibody. The immunized horses are bled or subjected to plasmaphoresis according to conventional techniques. Alternatively, or in addition, preparations without adjuvant can be used with other routes of immunization.

These bleedings must be treated to isolate the hepatitis antibody in anticipation of the final immunoabsorption purification step. Broadly, this preliminary purification is accomplished in three steps. First, plasma from the host animal is recalcified. Second, the serum is mixed with a sufficient amount of normal human plasma (NHP) to precipitate antibodies other than those associated with hepatitis by inducing insoluble antigen-antibody complex formation. The absorbed antiserum is assayed for hepatitis antibody using CEP. Third, the antibody reactive with antigens associated with hepatitis is precipitated with ammonium sulfate. This material can be frozen until used.

Preparation of Charcoal Immunoabsorbent Column

The preparation of the purified antibody which is conjugated to produce the reagents of this invention is accomplished by subjecting the hepatitis antibody produced as disclosed above to an immunospecific extraction process. For a general discussion of this procedure, reference should be made to British Pat. No. 1,287,625 to Bradish et al., Mar. 19, 1975, entitled *Immunodpecific Separation of Antigens and Antibodies,* the disclosure of which is incorporated herein by reference.

In general, this purification process as utilized in the present invention, takes advantage of the ability of antibodies reactive with hepatitis antigens to complex with these antigens to the exclusion of other extraneous antibodies and proteins which are inevitably present in the antibody sample extracted from the bleedings.

A column is prepared by packing prewashed, sorbent carbon into a glass or plastic tube by using conventional techniques. A pool of antigen is prepared from at least six individual serum specimens to obtain a diverse mixture of hepatitis antigens. The pool is then adjusted to a protein concentration of between 1 and 2 mg protein per ml solvent, based on UV absorption.

To attach the antigen onto the carbon, this diluted solution is introduced at a flow rate within the range of 300 to 1,000 ml per hour. Seventy five mg protein should be added per gram of charcoal in the column. The effluent from the column is collected in 500 ml aliquots, each of which are checked for protein content. The column is considered saturated with the antigen when the effluent has a protein content approximately equal to that of the starting material. The bed is washed by flowing phosphate buffered saline (PBS) through the column until the effluent shows no appreciable detectable absorption at 280 nm.

To elute any loosely attached protein, the charcoal bed is flushed with freshly prepared 5M sodium iodide solution containing 200 mg per liter of sodium thiosulfate. Afterwards, the sodium iodide solution is flushed from the column by running a sufficient volume of PBS therethrough. After a final washing of the bed with PBS containing 1 mg per ml sodium azide (preservative), the column can be stored at 2°-8° C. until ready for use.

The antibody, purified and described above, is freed of ammonium sulfate and diluted with PBS on the basis of 1 part antibody to 2 parts buffer. The column is set up and situated so that fractions can be collected. The antibody solution is added continuously to the column with a flow rate of about 200 ml/hour. Effluent is collected and tested for protein and hepatitis antibody content to determine when the column is saturated with antibody. After saturation is achieved, the column bed is washed with PBS to remove loosely absorbed protein.

At this point, antigens immobilized on the charcoal column have formed a bond with the antibodies reactive with them. Other extraneous proteins and antibodies, nonspecific to the absorbed antigens have passed through the column and have been separated from the antibody.

To break this antibody-antigen bond, and to elute the purified antibody, a 5M solution of NaI prepared immediately prior to use is introduced into the column. The volume of NaI solution used should be sufficient to remove all antibody bound to the column. With the flow rate of the column set at least 200 ml per hour, the eluate is collected in fractions of appropriate volumes. The total amount collected should be at least equal to the volume of sodium iodide solution added.

As each fraction of the purified antibody is collected it is subjected to a dual filtration; first, through a 0.45 membrane, and second, through a 0.22 membrane. The filtrate is diluted 1:3 using distilled water at 2°–8° C., e.g., 200 ml of filtrate is added to 400 ml of distilled water. These diluted antibody fractions are then added to, for example, an AMICON concentrator equipped with an XM-50 membrane, and the fractions are concentrated.

As a last purification step, the concentrated, purified, antibody is dialyzed. Following dialysis, the antibody is removed and centrifuged. The supernatant is dialyzed for at least 24 hours against 0.01M sodium phosphate solution, as compared to against PBS in the first dialysis. After completion of this final dialysis, protein concentration of the antibody is measured.

The antibody is then assayed for activity against the standard antigen according to the CEP technique to determine antibody content and, if found acceptable, is lyophilized and stored until used.

Bonding Antibody to Insoluble Member

The next step in the preparation of the reagents is to covalently bond a first portion of purified antibody to an insoluble member. To effect this bonding, the insoluble member used must be provided with reactive groups or sites capable of reacting with the specific antibody used in the bioassay.

The preparation of the insoluble member and the bonding of the antibody thereto is disclosed in detail below.

U.S. Pat. No. 3,700,609 entitled *Graft Copolymers*, to G. W. Tregear et al., the disclosure of which is incorporated herein by reference, discloses an insoluble continuous polymeric substance comprising a polymeric backbone onto which side chains of another polymer or copolymer are grafted. By suitable choice of the grafted polymer, it is possible to chemically link biological substances to the insoluble substrate. A product which is disclosed in the above patent is commercially available in a disc form under the tradename PROTAPOL DI/1 from Imperical Chemical Industries of Australia and New Zealand (ICIANZ).

The PROTAPOL DI/1 comprises a polytetrafluoroethylene backbone having isothiocyanopolystyrene groups grafted uniformly over its surface and is designed for use in radioimmunoassay. The discs, as presently available, are approximately 0.01 inches thick and 0.5 inches in diameter.

Figure 8:
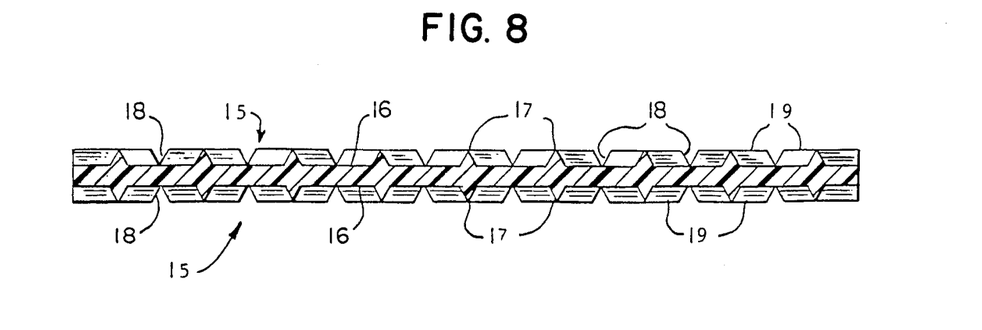
FIG. 8 is a cross-sectional view of the disc of FIG. 7.

In accordance with one important embodiment of the present invention, each disc is provided with a waffle-like pair of surfaces 15 comprising a first series of linear ridges 17 and a second series of linear ridges 19 which form grids. Ridges 17 and 19 are preferably perpendicular to each other and hence define a plurality of square depressions 16. As seen in FIG. 8 the sides of each ridge 17 and 19 taper upwardly from adjacent pairs of depression 16 to form a line defining the top of the ridge. It should be noted that in order to facilitate the description of the invention, the ridges 17 and 19 are greatly exaggerated in the drawing.

The desired configuration of the disc is achieved by passing the disc through rollers having projections on the surface of the rollers designed to impart the desired configuration on the disc. As is obvious, the rollers are designed to provide a sufficient amount of pressure to disfigure the polymeric material in the disc without actually puncturing the disc. This fact is important because it should be noted that the disc has a reactive layer on its surface. Thus, penetration of the disc would expose the teflon to which no antibody can be bonded. Exposure of the teflon layer would actually result in a disc which would have a lower bonding capacity.

The main consideration is to provide a disc matrix with surfaces which, when placed in a flat bottomed vial, will be substantially in complete contact with the test sample, i.e., there should be a minimum of surface-to-surface contact between the matrix and the bottom of the vial. In another important embodiment of the invention, the disc is configured to have a field of high points and low points.

The hepatitis antibody which is to be attached to this insoluble solid is preferably prepared as disclosed above. This purified hepatitis antibody must be attached to the disc such that its immuno-reactive groups remain accessible, and its activity is not altered by the attachment process.

The antibody, which typically has been preserved in the lyophilized state, is reconstituted by adding 100 ml of 0.1M $NaHCO_3$ (pH 9.6) for each 5.0 mg of antibody. In general, the procedure for attachment involves contacting 100 waffled discs with the dilute solution at 2°–8° C. for 8–16 hours, with agitation. Afterwards, the antibody solution is discarded and the discs are washed twice with successive volumes of 0.1M $NaHCO_3$, pH 9.6, phosphate buffered saline with 0.5% TWEEN 20. After an additional washing with crystalline bovine serum albumin, and freezing over dry ice, lyophilization is carried out and discs are stored at 2°–8° C. until ready for use.

Although the description in this specification relates to the preparation of discs having hepatitis antibody bonded thereto, it should be apparent to those skilled in the art that the disc of the present invention is useful to immobilize an almost limitless number of proteins. For example, the increased contact between the test sample and the disc enables the disc to be used in tests which involve the bonding of the following proteins thereto: antibodies to drugs such as digoxin, opiates, steroids; antibodies to natural products, for example insulin and other hormones; and, specific enzymes to metabolites found in blood and other body fluids.

EXAMPLE

The following procedure was used to prepare 8,000 discs, each of which were first treated with the press to produce the desired configuration as described. A batch of 8,000 discs requires 40 mg of hepatitis antibody, i.e., 5 mg per 1.000 discs. The protein content of the reconstituted hepatitis antibody is adjusted to 0.05 mg/ml in a final volume of 800 ml in 0.1M $NaHCO_3$ (ph=9.6). The entire 800 ml of buffered antibody is then added to a 1,000 ml screw-cap bottle provided with a leak proof liner containing the 8,000 discs, and the bottle is rotated for 16 hours, e.g., overnight, at 2°–8° C. to slowly tumble the discs through each rotation cycle. Afterwards, the liquid is poured from the bottle and discarded and the discs are transferred to a wide-mouth 2 liter flask.

The discs are washed twice with successive 1 liter volumes of cold (2°-8° C.) 0.1M NaHCO$_3$, pH 9.6, following which the buffer is removed. The discs are then washed again, this time using two successive 1 liter volumes of cold buffer (0.01M sodium phosphate, 0.15M NaCl, pH=7.4). After removing residual buffer, the discs are washed for a third time, using two successive one liter volumes of cold bovine serum albumin solution (0.3%).

The discs are finally washed with two successive 1 liter volumes of a solution of cold crystalline bovine serum albumin (pH=8) at a concentration of 2 mg/ml. This step is performed to provide a protein environment for the protein on the disc. The discs, after removing the residual wash, are then transferred to dishes or trays (9"×9"), each of which is lined with a sheet of filter paper and each of which contains 200 ml of the crystalline bovine serum albumin solution. When the transfer is complete, a sheet of filter paper is used to cover them. Buffer is thoroughly removed. The discs are then quick frozen for 10 minutes on dry ice.

The contents of the tray are then lyophilized. The dry discs are then removed and stored in stoppered containers.

Preparation of the Enzyme Tagged Antibody

An enzyme tagged or labeled antibody reactive with antigens is essential to the practice of the invention. Accordingly, a second sample of the antibody must be conjugated with a suitable enzyme. A preferred method of bonding a suitable enzyme to the purified antibody is disclosed in detail below.

Conjugating the Antibody With the Enzyme

Calf intestinal alkaline phosphatase is mixed with a solution of the reconstituted antibody in a ratio of 3:1, enzyme to antibody, to a final concentration greater than 10 mg of total protein per ml of solution in PBS (pH 7.4). The solution is dialyzed thoroughly to remove the NH$_4^{30}$ ions.

The dialyzed antibody enzyme mixture is then centrifuged to remove any insoluble material. The protein content of the supernatant is adjusted to 10 mg/ml by adding the PBS-Mg$^{++}$ solution. To this solution 8% glutaraldehyde is added on the basis of 1 ml glutaraldehyde solution per 10 ml antibody-enzyme solution. After stirring slowly for 3.5 to 20 minutes, during which time the antibody and enzyme are chemically linked by the glutaraldehyde, the solution of conjugate is dialyzed against PBS containing 0.001M Mg$^{++}$ to remove the glutaraldehyde.

The dialyzed material is then centrifuged and the supernatant is diluted by addition of an aqueous solution of 0.05M in tris (hydroxymethyl) aminomethane (pH 8) buffer, 1% normal human albumin (crystalline), 0.02% NaN$_3$, and 0.001M in MgCl$_2$.

The conjugate is then diluted 8 fold with PBS, aseptically filtered and dispensed into bottles in which it may be stored.

In addition to alkaline phosphatase, other enzymes are useable in the procedure of the present invention. Indeed, there is an almost limitless list of enzymes which can be covalently bonded to the antibody.

Preparation of Control Serum

In order to obtain meaningful data from the immunoassay, it is necessary to prepare negative and positive control sera for proper comparison with a given test sample. The preparation of these controls for antigens associated with hepatitis is disclosed in detail in U.S. Pat. No. 4,157,280, entitled *Test Set for Detecting the Presence of Antigens Associated with Hepatitis*, by Seymour P. Halbert et al., the teachings of which are incorporated herein by reference.

Three control sera are necessary for this practice of this invention. One of these is a negative control serum which tests negative for antigens. The second control is a strong positive control which gives maximum reading in the test. The third control is weak positive control serum which is adjusted to give a reading about ⅓ to ½ the maximum reading and is adjusted by the addition of negative control serum.

Preparation of Substrate

The substrate for the enzyme reaction in the test is p-nitrophenylphosphate which is dissolved to a concentration of 1 milligram per ml in sodium carbonate buffer, the concentration of which is 0.028 molar sodium carbonate and 0.001 molar magnesium (pH=9.8).

Other Enzymes and Substrates

At this point, it should be noted that other substrates and their buffering agent and pH appear in Table I below.

TABLE I

| | |
|---|---|
| β-glycerol phosphate | (serum), 7.4 |
| β-glycerol phosphate | barbital, 8.6 |
| phenyl phosphate | carbonate-bicarbonate, 9-10 |
| β-naphthyl phosphate | barbital, 9.1 |
| p-nitrophenyl phosphate | 2A2M1P, 10.25 |
| phenolphthalein phosphate | 2A2M1P, 9.90 |
| p-nitrophenyl phosphate | 2A2M1P, 10.17 |
| thymolphthalein phosphate | carbonate-bicarbonate, 10.0 |
| p-nitrophenyl phosphate | diethanolamine, 9.8 |
| 4-methylumbelliferyl phosphate | carbonate-bicarbonate, 9.2 |

It should be noted that the substrates indicated in Table I are all organic phosphate esters. It should be apparent that other organic phosphate esters could be used as substrates for the enzyme alkaline phosphatase.

In addition to alkaline phosphatase, other enzymes are useable in the procedure of the present invention. Indeed, there is an almost limitless list of enzymes which can be covalently bonded to the antibody. A representative list of such enzymes and their substrates appear below.

Of the various enzymes, the following table indicates enzymes of particular interest set forth in accordance with the I.U.B. classification.

1. Oxidoreductases
    1.1 Acting on the CH-OH group of donors
        1.1.1 With NAD or NADP as acceptor
            1. alcohol dehydrogenase
            6. glycerol dehydrogenase
            26. glyoxylate reductase
            27. L-lactate dehydrogenase
            37. malate dehydrogenase
            49. glucose 6-phosphate dehydrogenase
            17. mannitol 1-phosphate dehydrogenase
        1.1.2. With cytochrome as an acceptor
            3. L-lactate dehydrogenase 1.1.3. With $O_2$ as acceptor
    4. glucose oxidase
    9. galactose oxidase
1.2. Acting on the $CH-NH_2$ group of donors
    1.4.3 With $O_2$ as acceptor
        2. L-amino acid oxidase
        3. D-amino acid oxidase
1.6 Acting on reduced NAD or NADP as donor
    1.6.99 With other acceptors diaphorase
1.10 Acting on diphenols and related substances as donors
    1.10.3 With $O_2$ as acceptor
        1. polyphenol oxidase
        3. ascorbate oxidase
1.11 Acting on $H_2O_2$ as acceptor
    1.11.1
        6. catalase
        7. peroxidase
3. Hydrolases
    3.1 Acting on ester bonds
        3.1.1 Carboxylic ester hydrolases
            7. cholinesterase
        3.1.3 Phosphoric monoester hydrolases
            1. alkaline phosphatase
        3.1.4 Phosphoric diester hydrolases
            3. phospholipase C
    3.2 Acting on glycosyl compounds
        3.2.1 Glycoside hydrolases
            1. a-amylase
            4. cellulase
            17. lysozyme
            23. β-galactosidase
            27. amyloglucosidase
            31. β-glucuronidase
    3.4 Acting on peptide bonds
        3.4.2 Peptidyl-amino acid hydrolase
            1. carboxypeptidase A
        3.4.4 Peptidyl-peptide hydrolase
            5. a-chymotrypsin
            10. papain
    3.5 Acting on C—N bonds other than peptide bonds
        3.5.1 In linear amides
            5. urease
    3.6 Acting on acid anhydride bonds
        3.6.1 In phosphoryl-containing anhydrides
            1. inorganic pyrophosphatase
4. Lyases
    4.1 Carbon-carbon lyases
        4.1.2 Aldehyde lyases
            7. aldolase
    4.2 Carbon-oxygen lyases
        4.2.1 Hydrolases
            1. carbonic anhydrase
    4.3 Carbon-nitrogen lyases
        4.3.1 Ammonia lyases
            3. histidase The enzyme that is used for tagging the antibody is selected with several considerations in mind. These considerations include the stability of the enzyme, the ease of assay of the enzyme, the ability of the enzyme to withstand the conditions of the covalent bonding to the antibody, the ease of availability of the enzyme, and the cost of the enzyme.

Performance of Test for Detection of Hepatitis

Five controls should be assayed with each group of unknowns—three negative controls, one strong postive control, and one weak positive control. These should be subjected to the same process and incubation times as the test samples. Caution: Use a clean pipet or disposable tip for each transfer to avoid cross-contamination.

1. Preset water bath to 43° C.
2. Number two sets of vials to correspond to test sample identification and controls, and place vials in vial holders. The first set of these vials will be used for the incubation of test specimens and controls with the antibody coated disc and with the antibody-enzyme tagged reagent. The second set of vials will be used in Step 12 for the substrate reaction.
3. Pipet 0.05 ml (one drop) of horse globulin reagent into the bottom of the first set of vials. Nonspecific false positives resulting from antibodies present in certain human sera which react with horse globulin, advantageously, are essentially eliminated by using horse globulin in the test sample diluent.
4. Into this first set of vials pipet 0.5 ml of each test sample into the bottom of the vial having the corresponding sample identification; pipet 0.5 ml of the positive and negative controls into the bottom of their respective vials.
5. Transfer an antibody—coated disc to each vial of the first set. Keep the surface of the discs clean. They should be transferred with clean forceps or a suction-tipped cannula. They should not be handled with the fingers.
6. Incubate the vials at 43° C. in a water bath with shaking attachment set for mild agitation for 30 minutes.
7. After incubating the sample with the antibody disc, completely aspirate all supernatants from each vial. Wash the discs by adding 2.5 ml of isotonic saline solution to all the vials, then completely aspirate the fluid from all of the vials. Repeat this procedure so that each disc is washed two times. To aid in removing all fluid, tilt the vial holder while aspirating. Shake the vial holder after each addition of wash solution. The liquid waste collected in the container attached to the aspirator should be autoclaved before disposal (minimum of one hour at 121° C.).
8. After final wash and aspiration, add 0.3 ml of the enzyme-labeled antibody solution to each vial.
9. Incubate the vials for one hr. at 43° C. in the water bath with the shaking attachment set for mild agitation.
10. Prepare p-nitrophenyl phosphate substrate by rinsing the contents of one vial of p-NPP (100 mg) into 100 ml of diluted substrate buffer. (The latter is prepared by adding 10 ml of concentrated sodium bicarbonate buffer to 90 ml of distilled water.) Rotate gently to mix; solution should occur immediately.

Note: This substrate solution must be prepared on the day it is to be used. When not being used it should be refrigerated. Any solution remaining after 24 hours should be discarded.

11. Aspirate the supernatant and wash three times as in Step 7.
12. Transfer the discs to the second set of identically numbered clean vials prepared in Step 2.
13. To each vial containing a disc, add 2.5 ml of the p-nitrophenyl phosphate substrate solution prepared in Step 10.
14. Incubate vials for one hour at 43° C. in a water bath with the shaking attachment set for mild agitation.
15. Add two drops of 3M sodium hydroxide solution (approximately 0.1 ml total) to all the vials to terminate the reactions. Shake vials in holder to mix reagents well. The absorption readings must be made within four hours after terminating the reactions.

16. Pool the three negative controls and read the absorption at 405 nm in a photometer against a blank of distilled water. Record the result as absorbance units×1000. If the negative control reads greater than 600, the assay is unsatisfactory and must be repeated. When a flow-through photometer is used and strong positive samples are encountered, the cuvette should be rinsed with distilled water before reading the absorbance of the next sample. When nondisposable cuvettes are used, the cuvetter must be rinsed with distilled water following any positive reading.

17. With the pooled negative control, adjust the instrument to 0 absorbance. Determine the absorbance of each reaction mixture, recording the results as absorbance units×1000.

With some photometers, the instrument cannot be adjusted to 0 with the pooled negative control samples. In this case, the reading of the negative controls must be subtracted from the reading of each sample.

Evaluation of Results

Unknown test samples whose absorbance units×1000 values are greater than 100 are considered to be reactive, using the pooled negative controls as a blank. It may be desired to repeat the test on samples considered reactive. Before classifying a reactive serum as positive for antigens associated with hepatitis, confirmation must be obtained by testing with the Cordis Confirmatory Test Set (Cat. No. 783-950). This assay must be performed on all reactive samples. A reactive serum, confirmed by neutralization with horse antiserum, must be considered positive for hepatitis B antigen. As is noted above, confirmation testing is required in order to evaluate the results. Confirmation testing is required by the Food and Drug Administration as well as by the laws of many states. Briefly, confirmation testing in accordance with the present invention is accomplished as follows:

The positive test sample is tested in duplicate. After the first step in which the sample is exposed to the disc in each vial, following washing, one disc is exposed to antibodies specific for the hepatitis antigens; and, the other disc is exposed to normal horse serum. After one half hour of incubation, the subsequent procedures are identical to those carried out in the routine screening assay. If a sample is positive for hepatitis, the specimen which was exposed to the horse antibody will have a very low value; whereas, the disc exposed to the normal horse serum will have a high value equivalent to that found in the routine screening procedure.

Samples which have low concentrations of the hepatitis antigen, tend to have low final read out values. Those which have a high concentration of hepatitis antigens will have maximum values. Within a narrow range of concentration differences, the resulting read out optical densities will tend to give quantitative information concerning the concentration of hepatitis antigens present in the sample.

Limitations to the Procedure

1. Nonrepeatable reactives: If repeat testing on a reactive sample shows the value is less than the 100 cutoff value, the test is presumed to be a nonrepeatable reactive and is considered negative for antigens associated with hepatitis. The original result may be due to errors in technique, such an inadequate washing.

2. Nonspecific positives: The nonspecific false positives resulting from antibodies present in certain human sera that react with horse globulin are essentially eliminated by using horse globulin in the test sample diluent.

3. Plasma from blood collected in EDTA should not be used.

It should be noted that the incubation periods for various steps and the temperature at which incubation is performed can be accomplished over a wide range of times and temperatures. Thus, this invention is not intended to be limited in any way to the time and temperature of incubation. For example, the time of the incubation of the insoluble member with the sample may range between 10 minutes and 24 hours, with the temperature of incubation ranging between 2° C. and 50° C. On the other hand, the time of incubation of the insoluble member with the enzyme tagged binding partner ranges between 30 minutes to 24 hours, with the temperature of incubation of the insoluble member with the enzyme tagged binding partner ranging between 2° C. and 50° C.

It should also be noted that the process of the present invention can be used to determine the presence of antigens associated with hepatitis in any body fluid where the antigens are present. Thus the process can be used to determine the presence of these antigens in serum, plasma, components of plasma, components of serum, urine, saliva, and cerebrospinal fluid.

Results

A representative showing of the results of tests performed in accordance with the present invention appear below. The results shown in Table A are the results of tests in accordance with the present invention for samples which test positive for hepatitis by the CEP method. The values given in Table B are the values for test samples which test positively for hepatitis by the radioimmunoassay method yet negative for hepatitis by the CEP method and the values given in Table C test negative for both the RIA and the CEP method. The numerical values given in Tables A, B and C for the various test samples are the values obtained by testing with the procedure of the present invention.

TABLE A

| Test Sample | CEP+ (O.D. × 1000) OD405 |
|---|---|
| 72 | 2807 |
| 73 | 2802 |
| 79 | 2815 |
| 82 | 2822 |
| 121 | 2831 |
| 201 | 2768 |
| 202 | 2780 |
| 205 | 2749 |
| 206 | 2758 |
| 208 | 2795 |
| 209 | 2800 |
| 210 | 2764 |
| 213 | 2776 |
| 214 | 2804 |
| 217 | 2795 |
| 218 | 2800 |
| 219 | 2746 |
| 220 | 2718 |
| 226 | 2695 |
| 228 | 2782 |
| 232 | 2760 |
| 234 | 2774 |
| 235 | 2764 |

TABLE A-continued

| | CEP+ | |
|---|---|---|
| Test Sample | | (O.D. × 1000) OD405 |
| 238 | | 2760 |
| 239 | | 2755 |
| 244 | | 2730 |
| 250 | | 2707 |
| 251 | | 2761 |
| 252 | | 2778 |
| 253 | | 2783 |
| 254 | | 2742 |
| 255 | | 2743 |
| 256 | | 2784 |
| 260 | | 2775 |

TABLE B

| | RIA+ CEP− | |
|---|---|---|
| Test Sample | | (O.D. × 1000) OD405 |
| 65 | | 2745 |
| 68 | | 2675 |
| 69 | | 2266 |
| 75 | | 1354 |
| 77 | | 265 |
| 81 | | 953 |
| 87 | | 1383 |
| 123 | | 1688 |
| 124 | | 2739 |
| 125 | | 1741 |
| 204 | | 285 |
| 243 | | 2466 |
| 261 | | 2636 |

TABLE C

| | Neg | |
|---|---|---|
| Test Sample | | (O.D. × 1000) OD405 |
| 88 | | 0 |
| 89 | | 0 |
| 90 | | 0 |
| 91 | | 23 |
| 92 | | 42 |
| 93 | | 0 |
| 94 | | 0 |
| 97 | | 38 |
| 98 | | 0 |
| 99 | | 0 |
| 100 | | 0 |
| 101 | | 0 |
| 102 | | 0 |
| 103 | | 0 |
| 104 | | 0 |
| 203 | | 0 |
| 207 | | 0 |
| 211 | | 8 |
| 212 | | 0 |
| 215 | | 0 |
| 216 | | 0 |
| 224 | | 0 |
| 225 | | 0 |
| 227 | | 0 |
| 229 | | 0 |
| 230 | | 0 |
| 231 | | 0 |
| 233 | | 45 |
| 240 | | 0 |
| 241 | | 0 |
| 242 | | 0 |

The invention may be embodied in other specific forms without departing from the spirit or essential characteristics thereof. The present embodiment is therefore to be considered in all respects as illustrative and not restrictive, the scope of the invention being indicated by the appended claims rather than by the foregoing description, and all changes which come within the meaning and range of equivalency of the claims are therefore intended to be embraced therein.

What is claimed is:

1. A method for detecting an antigen in a test serum containing said antigen, comprising the steps of:
   a. providing a first quantity of an antibody associated with an antigen, said first quantity of said antibody being covalently bound to a water-insoluble, water insuspensible, solid carrier;
   b. contacting and incubating a test serum containing said antigen with said antibody covalently bound to said water-insoluble, water-insuspensible solid carrier of step (a) whereby said antigen reacts with said antibody covalently bound to said solid carrier to immobilize said antigen;
   c. providing a solution of a second quantity of said antibody, said second quantity of said antibody being covalently linked to an enzyme;
   d. contacting and incubating said immobilized antigen resulting from step (b) with said solution of enzyme-linked antibody of step (c) whereby said enzyme-linked antibody reacts with said immobilized antigen to immobilize said enzyme-linked antibody;
   e. separating the solid carrier from the solution of enzyme-linked antibody;
   f. contacting and incubating said immobilized enzyme-linked antibody with a substrate solution wherein said enzyme linked to said antibody catalyzes a reaction of said substrate and produces a detectable reaction product; and
   g. correlating said detectable reaction product to the presence of said antigen to be detected.

2. The method of claim 1 wherein said solid carrier is a plastic disk.

3. The method of claim 1 wherein after said test serum is contacted and incubated with said water-insoluble, water-insuspensible solid carrier, said solid carrier is washed.

4. The method of claim 3 wherein after said immobilized antigen is contacted with said enzyme-linked antibody, said solid carrier is washed.

5. A method for detecting a viral antigen in a test serum containing said viral antigen, comprising the steps of:
   a. providing a first quantity of an antibody associated with a viral antigen, said first quantity of said antibody being covalently bound to a water-insoluble, water-insuspensible, solid carrier;
   b. contacting and incubating a test serum containing said viral antigen with said antibody covalently bound to said water-insoluble, water-insuspensible solid carrier of step (a) whereby said viral antigen reacts with said antibody covalently bound to said solid carrier to immobilize said viral antigen;
   c. providing a solution of a second quantity of said antibody, said second quantity of said antibody being covalently linked to an enzyme;
   d. contacting and incubating said immobilized viral antigen resulting from step (b) with said solution of enzyme-linked antibody of step (c) whereby said enzyme-linked antibody reacts with said immobilized antigen to immobilize said enzyme-linked antibody;
   e. separating the solid carrier from the solution of enzyme-linked antibody;

f. contacting and incubating said immobilized enzyme-linked antibody with a substrate solution wherein said enzyme linked to said antibody catalyzes a reaction of said substrate and produces a detectable reaction product; and g. correlating said detectable reaction product to the presence of said viral antigen to be detected.

6. The method of claim 5 wherein said solid carrier is a plastic disc.

7. The method of claim 5 wherein after said test serum is contacted and incubated with said water-insoluble, water-insuspensible solid carrier, said solid carrier is washed.

8. The method of claim 7 wherein after said immobilized antigen is contacted with said enzyme-linked antibody, said solid carrier is washed.

9. A process for determining the presence of an antigen in a sample comprising the following steps:

(a) incubating the sample with an antibody immobilized on an insoluble member, the antibody being reactive with the antigen, the incubation enabling a bond to be formed between the antibody and the antigen present in the sample to produce an insoluble member having antigen bonded thereto in the event the antigen is present in the sample;

(b) separating the insoluble member from any unbonded substances;

(c) incubating the insoluble member with a solution containing a tagged antibody reactive with the antigen, the tagged antibody being tagged with an enzyme capable of effecting a reaction of a substrate to produce a detectable reaction product, the incubation being conducted to enable the tagged antibody to bond to any antigen bonded in step (a) to the antibody on the insoluble member;

(d) separating the insoluble member from the enzyme tagged antibody solution to remove any unbonded tagged antibody therefrom;

(e) exposing the insoluble member to a substrate solution which the enzyme of the tagged antibody reacts upon to enable a chemical change in the substrate to take place and to produce a detectable reaction product; and, (f) detecting any reaction product present in the solution to determine the presence of the antigen.

10. The process as set forth in claim 9 wherein the reaction product is detected by measuring the optical absorption of the substrate solution.

11. The process as set forth in claim 9 wherein the insoluble member is a polymeric member having said immobilized antibody covalently bonded to its surface.

12. The process as set forth in claim 9 wherein the antigen is a viral antigen.

13. The process as set forth in claim 9 wherein the enzyme is alkaline phosphatase.

14. The process as set forth in claim 13 wherein the substrate is p-nitrophenyl phosphate.

15. The process as set forth in claim 9 wherein the value obtained in detecting any reaction product is compared with the value obtained from at least one sample known to contain the antigen.

16. The process as set forth in claim 15 wherein the comparison of values is quantitative.

17. The process as set forth in claim 9 wherein the sample incubated in step (a) is a body fluid.

18. The process as set forth in claim 17 wherein the antigen is a viral antigen.

* * * * *

REEXAMINATION CERTIFICATE (1255th)

United States Patent [19]

Halbert et al.

[11] B1 4,642,285

[45] Certificate Issued Apr. 17, 1990

[54] SANDWICH EIA FOR ANTIGEN

[75] Inventors: Seymour P. Halbert, Miami; Milton Anken, N. Miami Beach, both of Fla.

[73] Assignee: Diamedix Corporation, Miami, Fla.

Reexamination Request:
No. 90/001,695, Jan. 24, 1989

Reexamination Certificate for:
Patent No.: 4,642,285
Issued: Feb. 10, 1987
Appl. No.: 606,122
Filed: May 2, 1984

Related U.S. Application Data

[63] Continuation of Ser. No. 617,743, Sep. 29, 1975, Pat. No. 4,474,878.

[51] Int. Cl.$^4$ .............. G01N 33/53; G01N 33/535; G01N 33/545; G01N 33/576
[52] U.S. Cl. ......................... 435/7; 422/56; 422/58; 435/5; 435/805; 435/810; 435/21; 436/811; 436/531; 436/532; 436/820
[58] Field of Search ............ 435/5, 7, 21, 805, 810; 422/56, 58; 436/531, 532, 820, 811

[56] References Cited

U.S. PATENT DOCUMENTS

| | | | |
|---|---|---|---|
| 3,791,932 | 2/1974 | Schuurs et al. | 435/7 |
| 3,867,517 | 2/1975 | Ling | 436/531 |
| 4,016,043 | 4/1977 | Schuurs et al. | 435/7 |

OTHER PUBLICATIONS

N. A. Posch et al., Final Report, Detection of Hepatitis in Blood, NIH-NHLI-71-2350, National Technical Information Service, U.S. Department of Commerce, Sep., 1973.
van Weemen and Schuurs, Immunoassay Using Antibody-Enzyme Conjugates, FEBS Letters, vol. 43, No. 2, pp. 215-218 (Jul. 1974).
Belanger et al., Enzyme-Linked Immunoassay for Alpha-Fetoprotein by Competitive and Sandwich Procedures, Clinica Chimica Acta, vol. 48, pp. 15-18 (1973).

*Primary Examiner*—Catherine M. Nucker

[57] ABSTRACT

A sensitive direct immunoassay system is provided for the detection of an antigen in body fluids. A single antibody which reacts with an antigen or antigens and which is bonded to an insoluble member, is incubated with a test sample. During this first period of incubation a portion of an antigen present in the test sample will combine with the antibody immobilized on the insoluble member. The antibody bonded member, to which antigen is attached, is then washed and incubated with an enzyme tagged antibody reagent. During the second incubation, the tagged antibody reacts with antigen fixed to the antibody member in the first incubation. Thus, an immobilized "sandwich" is formed of an insoluble member- antibody-antigen-enzyme tagged antibody. After the second incubation, the member is washed again to remove unreacted enzyme antibody reagent. The member is then exposed to a substrate which is converted by the enzyme to produce an end product. The tagged antibody reagent will be fixed in the second incubation only if antigen was present in the sample. The amount of enzyme tagged antibody fixed is proportional to the amount of antigen or antigens present in the test sample up to the maximum capacity of the test. The concentration of the end product, and hence the amount of antigen or antigens, is determined by a spectrophotometer which measures the optical absorption of light by the end product. This readout is then compared against a standard value for both antigen negative and antigen positive samples.

REEXAMINATION CERTIFICATE ISSUED UNDER 35 U.S.C. 307

NO AMENDMENTS HAVE BEEN MADE TO THE PATENT

AS A RESULT OF REEXAMINATION, IT HAS BEEN DETERMINED THAT:

The patentability of claims 1-18 is confirmed.

* * * * *